United States Patent [19]

Gardner et al.

[11] 4,139,621

[45] Feb. 13, 1979

[54] N-(4-SUBSTITUTED-3,5-DICHLORO-PHENYL)-PIPERAZINES

[75] Inventors: Derek V. Gardner, Bishops Stortford; Alexander C. Goudie, Harlow, both of England

[73] Assignee: Beecham Group Limited, United Kingdom

[21] Appl. No.: 857,773

[22] Filed: Dec. 5, 1977

[30] Foreign Application Priority Data

Dec. 10, 1976 [GB] United Kingdom ............... 51611/76

[51] Int. Cl.$^2$ ................. C07D 295/14; C07D 295/20; C07D 295/12

[52] U.S. Cl. .................................. 424/250; 544/389; 544/391; 544/395

[58] Field of Search ................... 260/268 PH, 268 C; 544/389, 391, 395; 424/250

[56] References Cited

U.S. PATENT DOCUMENTS

| | | | |
|---|---|---|---|
| 3,775,313 | 11/1973 | Adams et al. | 210/62 |
| 3,988,456 | 10/1976 | Nishimura et al. | 260/268 PH |

*Primary Examiner*—Jose Tovar
*Attorney, Agent, or Firm*—Jacobs & Jacobs

[57] ABSTRACT

1-(3,5-Dichlorophenyl)piperazines bearing a fluoro, chloro, methyl, nitro, hydroxy, methoxy, cyano, amino, methylamino or dimethylamino substituent in the 4-position of the phenyl ring and being further optionally substituted in the 4-position of the piperazine ring by tetrahydropyranyl, alkyl, formyl, carboxy, alkanoyl or carboalkoxy, and the acid addition salts thereof, are tranquilizers. A typical embodiment is 1-(3,4,5-trichlorophenyl)piperazine hydrochloride.

25 Claims, No Drawings

N-(4-SUBSTITUTED-3,5-DICHLORO-PHENYL)-PIPERAZINES

DETAILED DESCRIPTION

The present invention relates to phenylpiperazines, to their preparation and to compositions containing them.

U.S. Pat. Spec. No. 3,637,705 disclosed that the compounds of the formulae (I) and (II):

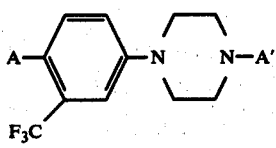

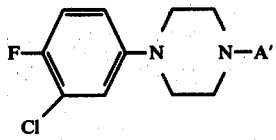

wherein A is F, Cl or Br and A' is H or tetrahydropyranyl have unusually strong anorexigenic properties. We have found that other phenylpiperazines may be prepared that have different pharmacological properties, namely tranquillizing activity.

Accordingly the present invention provides the compounds of the formula (III):

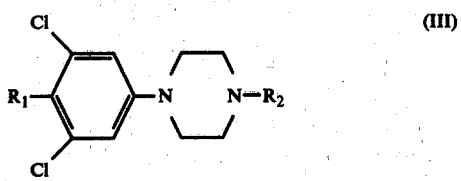

wherein $R_1$ is F, Cl, $CH_3$, $NO_2$, OH, $OCH_3$, CN, $NH_2$, $NH.CH_3$ or $N(CH_3)_2$ and $R_2$ is a hydrogen atom or a tetrahydropyranyl group or a $C_{1-4}$ alkyl group or a group $CO.R_3$ or $CO_2R_3$ where $R_3$ is a hydrogen atom or a $C_{1-4}$ alkyl group; and acid addition salts thereof.

One particularly suitable group of compounds of the formulae (III) are those of the formulae (IV):

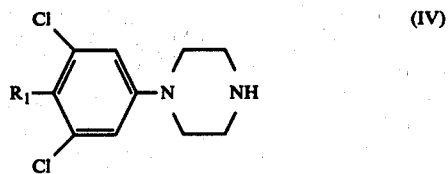

and acid addition salts thereof wherein $R_1$ is as defined in relation to formula (III).

Another particularly suitable group of compounds of the formulae (III), are those of the formulae (V):

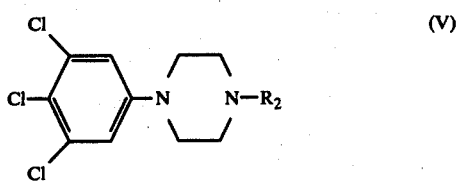

wherein $R_2$ is as defined in relation to formula (III) and acid addition salts thereof.

Particularly suitable values for $R_1$ for inclusion in the compounds of the formulae (III) and (IV) include F, Cl, $CH_3$, OH and $OCH_3$, especially F, Cl and $CH_3$.

Suitable values for $R_2$ for inclusion in the compounds of the formulae (III) and (V) include the hydrogen atom and the methyl, ethyl and $CO_2R_3$ groups.

A particularly suitable value for $R_2$ for inclusion in the compounds of the formulae (III) and (V) is the hydrogen atom.

The preferred compounds of this invention is that of the formula (VI):

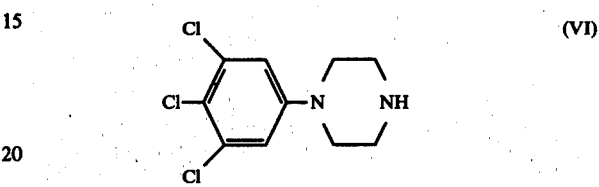

and its pharmaceutically acceptable acid addition salts.

Acid addition salts of the compounds of the formulae (III)–(VI) will normally be those with pharmaceutically acceptable inorganic or organic acids such as hydrochloric, hydrobromic, sulphuric, orthophosphoric, methanesulphonic, toluenesulphonic, acetic, propionic, succinic, salicylic, acetylsalicylic, ascorbic, lactic, citric, gluconic, tartaric and the like.

The present invention also provides pharmaceutical compositions which comprise a compound of the invention and a pharmaceutically acceptable carrier.

The compositions of the invention are specially useful in treating adverse mental states such as, for example, psychoses or anxiety states. For such treatment, the compounds are generally administered orally although parenteral methods of administration may also be used.

Typical oral formulations will include tablets, pills, capsules, sachets, granules, powders, suspensions, emulsions and solutions. Particularly suitable oral formulations are tablets and capsules. Where appropriate, the formulations may include conventional diluents, binding agents, dispersing agents, surface-active agents, lubricating agents, coating materials, flavouring agents, colouring agents, solvents, thickening agents, suspending agents, sweeteners or any other pharmaceutically acceptable additives, for example, gelatin, lactose, starch, talc, magnesium stearate, hydrogenated oils, polyglycols and syrups. Where the formulations are tablets or capsules and the like, they will represent pre-measured unit doses but in the case of granules, powders, suspensions and the like, the formulations may be presented as pre-measured unit doses or in multi-dose containers from which the appropriate unit dose may be withdrawn.

Injectable compositions may be as aqueous or non-aqueous solutions suspensions or emulsions in a pharmaceutically acceptable liquid (e.g. sterile pyrogen-free water or parenterally acceptable oils) or mixtures of liquids which may contain bacteriostatic agents, antioxidants or other preservatives, buffers, (preferably in the physiological pH range of 6.5–7.0), solutes to render the solution isotonic with the blood, thickening agents, suspending agents or other pharmaceutically acceptable additives. Such forms will be presented in unit dose forms such as ampoules or disposable injection devices or in multi-dose forms such as a bottle from which the appropriate dose may be withdrawn, or as a solid form or concentrate which can be used to quickly prepare an injectable formulation.

In general, the compositions of the invention will usually have associated with them, directions for use as anxiolytic or anti-psychotic medications.

Preferred dosage forms of the composition will be conventional tablets or capsules containing a pre-measured dose for oral administration. Such dosage forms will normally contain between 1 and 100 mgs. of compound of formula (III) and generally between 2.5 and 75 mgs. preferably from about 5 to about 50 mgs. Such dosage forms will normally be taken from 1 to 6 times daily. The maximum daily dose for a 70 kg. adult will not normally exceed 360 mgs. and will not usually exceed 250 mgs. A daily dose of not more than 150 mgs. is generally preferred. Normally, the daily dose for a 70 kg, adult will be at least 2.5 mgs., usually at least 5 mgs.

The compositions of the invention may be prepared by conventional methods of mixing, blending, tabletting and the like.

Normally the compound of the formula (III) used in the composition will be a solid and often an acid addition salt.

The present invention also provides a process for the preparation of compounds of the invention which process comprises the reaction of a compound of the formula (VII):

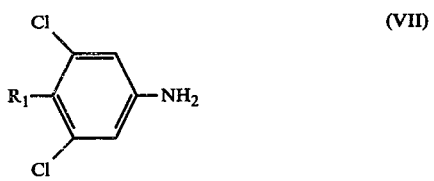

(VII)

wherein $R_1$ is a defined in relation to formula (III); with a compound of the formula (VIII):

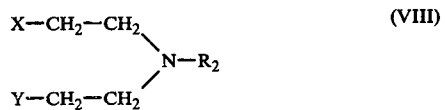

(VIII)

or an acid addition salt thereof wherein $R_2$ is hydrogen or a $C_{1-4}$ alkyl group and X and Y are groups readily displaced by nucleophiles and thereafter if desired when $R_2$ is hydrogen, acylating the resulting piperazine in known manner.

Suitable groups X and Y include I, Br, Cl, $OSO_2CH_3$, $OSO_2C_6H_4CH_3$, $OCO_2tC_4H_9$ and their chemical equivalents.

Most suitably the groups X and Y are both chlorine or bromine atoms.

The process of this invention will normally be carried out in an organic solvent such as a lower alkanol, for example ethanol, normal butanol or the like.

In general it is necessary to carry out the reaction at an elevated temperature for example 30°-150° C. although temperatures outside this range can be used. Favourably the reaction is carried out at a temperature of about 75°-130° C.

If desired an acid acceptor may be used to consume the acid liberated by the condensation. Suitable acid acceptors include sodium carbonate and potassium carbonate.

An alternative process involves reaction of a compound of the formula (VII) with a compound of the formula (VIII) or an acid addition salt thereof wherein $R_2$ is hydrogen or a $C_{1-4}$ alkyl group and X and Y are both hydroxyl groups in the presence of eitherconcentrated (37%) hydrochloric or concentrated (48–66%) hydrobromic acid.

In general it is necessary to carry out the reaction at an elevated temperature, for example 60°-300° C. Favourably the reaction is carried out at a temperature of about 160°-260° C.

It will be appreciated that this process could be interpreted as forming the compound of the formula (VIII) in situ prior to its reaction with the compound of the formula (VII).

The compounds of the formula (III) may be converted to their acid addition salts (usually mono salts) by reaction with an acid in conventional manner. Similarly, the free bases may be liberated by neutralisation in conventional manner.

This invention also provides a process for the preparation of those compounds of the formula (III) wherein $R_2$ is a group $COR_3$ or $CO_2R_3$ which comprises the acylation or carboalkoxylation in a known manner of the corresponding compound wherein $R_2$ is a hydrogen atom. Generally this involves the reaction of the appropriate piperazine derivative with $Cl.CO.R_3$ or $Cl.CO_2R_3$ or their chemical equivalent at a non-extreme temperature in a conventional organic solvent.

The present invention also provides a process for the preparation of those compounds of the formula (III) wherein $R_2$ is a hydrogen atom which process comprises the hydrolysis of a corresponding compound of the formula (III) wherein $R_2$ is a —CO.OA group such that CO.OA represents an esterified carboxyl group.

The preceding reaction is preferably carried out on a compound of the formula (III) wherein $R_1$ is chlorine.

The group A may be any convenient organic esterifying moiety but it is preferred to use a lower alkyl group such as a methyl, ethyl or like group or a benzyl or like group.

The hydrolysis may be effected by treatment with an acid, for example a mineral acid such as hydrobromic, hydrochloric or the like. Such reactions are frequently carried out at from about 0° to about 110° C., for example 15° to 100° C. and conveniently at the reflux temperature of the medium.

The compounds of the formula (III) where $R_2$ is CO.OA group may be prepared by the reaction of a compound of the formula (III) wherein $R_2$ is a benzyl group, with a compound of the formula $ZCO_2A$, wherein Z is a group readily displaceable by a nucleophile, for example, a chlorine atom.

Such reactions are suitably carried out in an inert solvent such as benzene or toluene at an elevated temperature, for example at the reflux temperature.

The compounds of the formula (III) wherein $R_2$ is a benzyl group may be prepared by the reduction of a corresponding compound of the formula (IX):

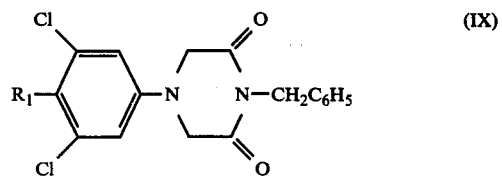

(IX)

wherein $R_1$ is as defined in relation to formula (III).

Such reductions may be brought about by the method of D. W. Henry, J. Het. Chem., 1966, Vol. 3, page 503 or by the general procedure of Description 3 herein.

The present invention also provides a process for preparing the compounds of the formula (III) wherein $R_2$ is an alkyl group which process comprises the alkylation of the corresponding compound wherein $R_2$ is a hydrogen atom.

Such reactions may be carried out by conventional methods of N-alkylating piperazines such as reaction with an alkyl iodide or the like in a solvent such as acetone.

This invention also provides a process for the preparation of compounds of the formula (III) wherein $R_2$ is a hydrogen atom, which process comprises the hydrogenation of the corresponding compound wherein $R_2$ is a hydrogenolysable group.

Suitable hydrogenolysable groups include benzyl and substituted benzyl groups.

Normally, the hydrogenation will be carried out in the presence of a transition metal catalyst, for example, palladium, at approximately atmospheric pressure.

EXAMPLE 1

1-(3,4,5-Trichlorophenyl)piperazine 3,4,5-Trichloroanaline (19.6g, 0.1 mole) and bis (2-chloroethyl) amine hydrochloride (17.8g, 0.1 mole) were dissolved in butan-1-ol (100 ml) and boiled under reflux for 2 days. The solution was allowed to cool and anhydrous potassium carbonate (13.8g, 0.1 mole) was added carefully and the resulting mixture was boiled under reflux with stirring for a further 2 days. The mixture was filtered hot and the filtrate allowed to cool to yield 1-(3,4,5-trichlorophenyl)piperazine hydrochloride (1.6g), m.p. 272°–275° C.

3,4,5-Trichloroanaline may be prepared by the method of S. N. Johary, S. S. Guha and P. C. Guha, *J. Indian Inst. Sci.*, 34, 287 (1952).

EXAMPLE 2

1-(3,4,5-Trichlorophenyl)-4-ethoxycarbonylpiperazine 1-(3,4,5-Trichlorophenyl)-4-benzylpiperazine (13.75g), dry toluene (350 ml) and ethyl chloroformate (31.21g) were refluxed together overnight. The reaction was cooled, diluted with water, the organic layer separated and washed with water (3 × 150 ml) till neutral, and finally washed with brine (1 × 150 ml). The organic layer was dried (anh. $Na_2SO_4$) and evaporated giving the intermediate ethyl carbamate as a pale brown solid (12.37g). The solid can be crystallised from ethanol as beige needles (m.p. 142°–143.5° C).

EXAMPLE 3

1-(3,4,5-Trichlorophenyl)piperazine hydrochloride 1-(3,4,5-Trichlorophenyl)-4-ethoxycarbonylpiperazine (12.3g) was refluxed with 48% hydrobromic acid (100 ml) overnight. The reaction was cooled, water added followed by aqueous sodium hydroxide solution (600 ml; 10%). The product was extracted into ether (3 × 100 ml), the ether extracts combined, washed with water (3 × 100 ml) till neutral, dried (anh. $Na_2SO_4$) and evaporated giving a brown oil which soon solidified (10.14g). The free base was converted to the hydrochloride (9.42g) by dissolving in dry ethanol and adding ethereal HCl till the hydrochloride precipitated out.

EXAMPLE 4

1-(3,4,5-Trichlorophenyl)-4-ethylpiperazine

To a stirred mixture of 1-(3,4,5-trichlorophenyl)piperazine (0.5g) and anhydrous potassium carbonate (0.26 g) in dry acetone (5 ml) was added, slowly, ethyl iodide (0.29g) and the resulting mixture was stirred under reflux for 2 hr. then filtered. Removal of the solvent gave a pale brown solid which was dissolved in ether and treated with ethereal hydrogen chloride to give 1-(3,4,5-trichlorophenyl)-4-ethylpiperazine hydrochloride (0.4g, 67%), m.p. 265°–270° (from ethanol-ether).

EXAMPLE 5

1-Acetyl-4-(3,4,5-trichlorophenyl) piperazine

A mixture of 1-(3,4,5-trichlorophenyl) piperazine (0.5 g) and acetic anhydride (0.4 ml) in ethanol (10 ml) was left to stand overnight at ambient temperature. The solvent was removed in vacuo and the residue was crystallised from ethyl acetate-light petroleum (b.p. 40°–60°) to give 1-acetyl-4-(3,4,5-trichlorophenyl) piperazine (0.43g, 76%), m.p. 133°–136°.

EXAMPLE 6

1-(3,5-Dichloro-4-methylphenyl) piperazine

A mixture of 3,5-dichloro-4-methylaniline (6g, prepared by the method of W. Davies, J. Chem. Soc. 1922, 806) and bis-2-chloroethylamine hydrochloride (6.05g) in n-butanol (25 ml) was stirred under reflux for 24 hr. Anhydrous potassium carbonate (4.69g) was added and the mixture was stirred under reflux for a further 48 hr. then filtered and allowed to cool. The resulting solid was removed by filtration and crystallised from ethanol-ether to give 1-(3,5-dichloro-4-methylphenyl) piperazine hydrochloride (0.82g) m.p. 280°–287°.

EXAMPLE 7

1-(3,5-Dichloro-4-methoxyphenyl) piperazine 3,5-Dichloro-4-methoxyaniline, m.p. 77°–79°, was prepared by the catalytic hydrogenation (10% Pd-C) of 2,6-dichloro-4-nitro-anisole in ethyl acetate at ambient temperature and atmospheric pressure.

A mixture of 3,5-dichloro-4-methoxyaniline (16.0g) and bis-(2-chloroethyl)amine hydrochloride (14.77g) in n-butanol (100 ml) was stirred under reflux for 48 hr. Anhydrous potassium carbonate (11.45g) was added and the resulting mixture was stirred under reflux for a further 24 hr., then filtered hot. The solid which precipitated on cooling was crystallised from ethanol-ether to give 1-(3,5-dichloro-4-methoxyphenyl)piperazine hydrochloride (3.7g) m.p. 252°–255°.

EXAMPLE 8

Demonstration of pharmacalogical effectiveness of 1-(3,4,5-Trichlorophenyl)piperazine 1-(3,4,5-Trichlorophenyl)piperazine hydrochloride [compound A] was tested in various conventional screens used for determining the effect of major tranquillizors. In these tests chlopromazine was used as a positive control. The results obtained were as follows:

|   | Compound A | Chlorpromazine |
|---|---|---|
| 1. Anti-Catapresan test (Mouse) | $ED_{50}$ 6 mg/kg p.o. | $ED_{50}$ 2.8 mg/kg p.o. |
| 2. Shuttlebox (Conditioned | | |

| | Compound A | Chlorpromazine |
|---|---|---|
| avoidance behaviour in the rat). % inhibition of crossing rate. | −73% at 5 mg/kg p.o. | −67% at 10 mg/kg p.o. |
| 3. Induction of catalepsy in the rat. | 0% at 40 mg/kg s.c. | 54% at 10 mg/kg i.p. |

The activity of Compound A in the anti-catapresan induced fighting test and the inhibition of conditioned avoidance responses in the shuttlebox tests indicate that Compound A has potential neuroleptic/anxiolytic activity in man. The lack of cataleptic activity suggests that Compound A will not induce the extrapyramidal side effects typical of neuroleptics of the chloropromazine type. The potency relative to chloropromazine in animal tests indicates that Compound A will be active in man at similar daily doses to chlorpromazine, that is 0.2–10 mg/kg orally.

EXAMPLE 9

Composition 1-(3,4,5-Trichlorophenyl)piperazine hydrochloride, magnesium stearate, microcrystalline cellulose and sodium starch glycollate may be blended together and granulated. These granules may then be used in a conventional rotary tabletting machine to produce 5000 tablets which on average contain the following:

| | |
|---|---|
| 1-(3,4,5-trichlorophenyl)- piperazine hydrochloride | 25 mg. |
| microcrystalline cellulose | 163 mg. |
| sodium starch glycollate | 10 mg. |
| magnesium stearate | 2 mg. |

EXAMPLE 10

1-(3,4,5-Trichlorophenyl)-piperazine 1-(3,4,5-Trichlorophenyl)-4-benzylpiperazine (1.71g.) in methanol (70 ml) was shaken with 10% Pd/C (0.17g.) under hydrogen at atmospheric pressure for 5.0 hrs. G.l.c. analysis of the reaction mixture demonstrated the presence of N-(3,4,5-trichlorophenyl)-piperazine (33%).

DESCRIPTION 1

N-Benzyliminodiacetic acid monocarbox-(3,4,5-trichlorophenyl)amide

N-Benzyliminodiacetic acid anhydride (31.87g) was dissolved in dry benzene (300 ml) and filtered through celite to remove any tarry material that might be present. This solution was then treated at room temperature with 3,4,5-trichloroaniline (27.57g) in dry benzene (200 ml). The N-benzyliminodiacetic acid monocarbox-(3,4,5-trichlorophenyl)-amide started to precipitate out almost immediately as a beige solid. The reaction mixture was warmed briefly and then left to cool. The product was isolated by filtration and washed with dry ether to remove any unreacted 3,4,5-trichloroaniline. It was obtained as a beige powder (38.27g).*
*(The anhydride may be produced by the method of D. W. Henry, J. H. et. Chem., 1966, vol. 3, page 503).

DESCRIPTION 2

1-(3,4,5-Trichlorophenyl)-4-benzylpiperazine-2,6-dione

N-Benzyliminodiacetic acid monocarbox-(3,4,5-trichlorophenyl)-amide (38.27g; 0.0953 moles) was heated at reflux in acetic anhydride (191.3g; 177 ml) for at least 0.5 hr. The excess acetic anhydride and acetic acid were removed in vacuo to give a brown crystalline solid (36.80g). The N-benzylpiperazinedione was crystallised from ethanol (850 ml) as pale brown needles (22.26g; m.p. 153.5°–154.5° C.). Concentration of the mother liquor gave a second crop (3.65g).

DESCRIPTION 3

1-(3,4,5-Trichlorophenyl)-4-benzylpiperazine

Aluminum chloride (38.93g) in dry ether (460 ml) — (CAUTION: exothermic reaction) — was added dropwise to lithium aluminum hydride (11.08g) suspended in dry ether (460 ml). During the addition, the reaction refluxed gently. N-Benzylpiperazinedione (22.26g) in dry tetrahydrofuran (170 ml) was then added to the lithium aluminum hydride/aluminum chloride mixture at such a rate as to maintain gentle refluxing. When the addition of the dione was completed the reaction was decomposed with aqueous sodium hydroxide solution (200 ml; 10%). The layers were separated and the aqueous layer was extracted with ether (3 × 200 ml). The combined organic layers were washed with water (3 × 200 ml) till neutral, dried (anh. Na$_2$SO$_4$) and evaporated to give a pale brown oil (16.87g; 96% purity by g.l.c.) with solidified upon cooling.

What we claim is:

1. A compound of the formula:

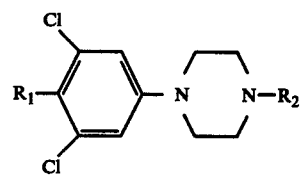

[(III)]

wherein R$_1$ is fluoro, chloro, methyl, nitro, hydroxy, methoxy, cyano, amino, methylamino or dimethylamino; and R$_2$ is hydrogen or tetrahydropyranyl, alkyl of 1 to 4 carbon atoms, CO.R$_3$ or CO$_2$R$_3$ wherein R$_3$ is hydrogen or alkyl of 1 to 4 carbon atoms;

or an acid addition salt thereof.

2. A compound of the formula:

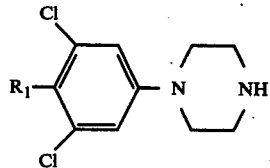

[(IV)]

or an acid addition salt thereof wherein R$_1$ is fluoro, chloro, methyl, nitro, hydroxy, methoxy, cyano, amino, methylamino or dimethylamino.

3. A compound of the formula:

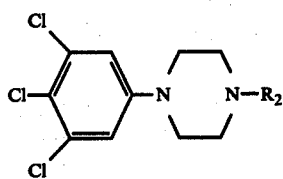

or an acid addition salt thereof wherein $R_2$ is as defined in claim 1.

4. A compound according to claim 2 wherein $R_1$ is fluoro, chloro, methyl, hydroxy or methoxy.

5. A compound according to claim 4 wherein $R_1$ is fluoro, chloro or methyl.

6. A compound according to claim 1 wherein $R_2$ is hydrogen, methyl, ethyl or $CO.R_3$ wherein $R_3$ is hydrogen or alkyl of 1 to 4 carbon atoms.

7. A compound according to claim 1 wherein $R_2$ is hydrogen or alkyl of 1 to 4 carbon atoms.

8. The compound of the formula

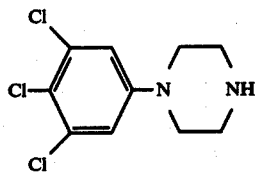

or a pharmaceutically acceptable acid addition salt thereof.

9. A compound according to claim 8 which is 1-(3,4,5-trichlorophenyl)piperazine.

10. A compound according to claim 8 which is a pharmaceutically acceptable acid addition salt of 1-(3,4,5-trichlorophenyl)piperazine.

11. A compound according to claim 8 which is 1-(3,4,5-trichlorophenyl)piperazine hydrochloride.

12. A compound according to claim 3 which is 1-(3,4,5-trichlorophenyl)-4-ethoxycarbonylpiperazine.

13. A compound according to claim 3 which is 1-(3,4,5-trichlorophenyl)-4-ethylpiperazine or a pharmaceutically acceptable acid addition salt thereof.

14. A compound according to claim 3 which is 1-acetyl-4-(3,4,5-trichlorophenyl)piperazine.

15. A compound according to claim 2 which is 1-(3,5-dichloro-4-methylphenyl)piperazine or a pharmaceutically acceptable acid addition salt thereof.

16. A compound according to claim 2 which is 1-(3,5-dichloro-4-methoxyphenyl)piperazine or a pharmaceutically acceptable acid addition salt thereof.

17. A pharmaceutical composition comprising a tranquillizing amount of a compound according to claim 1 and a pharmaceutically acceptable carrier.

18. A pharmaceutical composition comprising a tranquillizing amount of a compound according to claim 8 and a pharmaceutically acceptable carrier.

19. A composition according to claim 17 for oral administration to humans.

20. A composition according to claim 17 adapted for administration to humans by injection.

21. A composition according to claim 19 in unit dose form.

22. A composition according to claim 21 comprising from 1 to 100 mg of a compound according to claim 1.

23. A composition according to claim 21 comprising from 2.5 to 75 mg of a compound according to claim 1.

24. A composition according to claim 21 comprising from 5 to 50 mg of a compound according to claim 1.

25. A method of tranquillizing humans in need thereof which comprises administering a composition according to claim 17.

* * * * *